US 9,421,058 B2

(12) United States Patent
Nardini et al.

(10) Patent No.: US 9,421,058 B2
(45) Date of Patent: Aug. 23, 2016

(54) BONE FIXATION SYSTEM

(71) Applicant: DePuy Synthes Products, Inc., Raynham, MA (US)

(72) Inventors: Reto Nardini, Grenchen (CH); Robert Frigg, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/971,849

(22) Filed: Dec. 16, 2015

(65) Prior Publication Data

US 2016/0100877 A1   Apr. 14, 2016

Related U.S. Application Data

(62) Division of application No. 14/694,075, filed on Apr. 23, 2015, now Pat. No. 9,237,914, which is a division of application No. 13/078,188, filed on Apr. 1, 2011, now Pat. No. 9,039,683.

(60) Provisional application No. 61/417,614, filed on Nov. 29, 2010, provisional application No. 61/320,883, filed on Apr. 5, 2010.

(51) Int. Cl.
*A61B 17/16* (2006.01)
*A61B 17/88* (2006.01)
(Continued)

(52) U.S. Cl.
CPC ............ *A61B 17/8872* (2013.01); *A61B 17/16* (2013.01); *A61B 17/844* (2013.01); *A61B 17/864* (2013.01); *A61B 17/866* (2013.01); *A61B 17/8863* (2013.01); *A61B 18/22* (2013.01); *A61B 18/28* (2013.01);
(Continued)

(58) Field of Classification Search
CPC .......... A61B 18/18; A61B 17/04; A61F 2/02; A61F 2/28; A61F 2/30; B32B 7/04; A61C 8/00
USPC ........... 606/13, 232; 623/11, 16, 18; 428/343; 433/173
See application file for complete search history.

(56) References Cited

U.S. PATENT DOCUMENTS

| 4,784,135 A | 11/1988 | Blum et al. |
| 4,911,712 A | 3/1990 | Harrington |

(Continued)

FOREIGN PATENT DOCUMENTS

| CA | 1238690 | 6/1988 |
| CA | 2055526 | 5/1992 |

(Continued)

OTHER PUBLICATIONS

Cherrick et al., "Indocyanine Green: Observations on it's Physical Properties, Plasma Decay and Hepatic Extraction", Thorndike Memorial Laboratory and the Second and Fourth (Harvard) Medical Services, Boston City Hospital and the Department of Medicine, Harvard Medical School, Boston MA., Dec. 4, 1959.

*Primary Examiner* — William Thomson
*Assistant Examiner* — Victor Shapiro
(74) *Attorney, Agent, or Firm* — Baker & Hostetler LLP

(57) ABSTRACT

A bone fixation system is provided. The bone fixation system may include a plate, one or more fasteners configured to attach the plate to a target anatomical location such as bone, and a surgical device that facilitates the attachment of the plate and the fasteners.

20 Claims, 8 Drawing Sheets

(51) Int. Cl.
  *A61B 17/84* (2006.01)
  *A61B 17/86* (2006.01)
  *A61B 18/22* (2006.01)
  *A61B 18/28* (2006.01)
  *A61B 18/00* (2006.01)

(52) U.S. Cl.
  CPC ............. *A61B2018/00565* (2013.01); *A61B 2018/00601* (2013.01); *A61B 2217/007* (2013.01)

(56) References Cited

U.S. PATENT DOCUMENTS

| | | |
|---|---|---|
| 5,118,293 A | 6/1992 | Levy |
| 5,171,150 A | 12/1992 | Levy |
| 5,192,279 A | 3/1993 | Samuels et al. |
| 5,249,964 A | 10/1993 | Levy |
| 5,397,365 A | 3/1995 | Trentacosta |
| 5,796,903 A | 8/1998 | Tran |
| 6,343,174 B1 | 1/2002 | Neuberger |
| 6,802,838 B2 | 10/2004 | Loeb et al. |
| 7,335,205 B2 | 2/2008 | Aeschlimann et al. |
| 7,461,982 B2 | 12/2008 | Boutoussov et al. |
| 2003/0139735 A1 | 7/2003 | Neuberger |
| 2004/0166309 A1 | 8/2004 | Gong et al. |
| 2006/0282068 A1 | 12/2006 | Griffin et al. |
| 2007/0270833 A1 | 11/2007 | Bonutti et al. |
| 2007/0299449 A1 | 12/2007 | Allinniemi et al. |
| 2008/0039845 A1 | 2/2008 | Bonutti et al. |
| 2008/0047107 A1 | 2/2008 | Clinch et al. |
| 2008/0219629 A1 | 9/2008 | Rizoiu et al. |
| 2008/0275500 A1 | 11/2008 | Aeschlimann et al. |
| 2009/0024161 A1 | 1/2009 | Bonutti et al. |
| 2010/0241229 A1 | 9/2010 | Baehre et al. |
| 2012/0129131 A1 | 5/2012 | Baehre et al. |

FOREIGN PATENT DOCUMENTS

| | | |
|---|---|---|
| CN | 201126922 | 10/2008 |
| DE | 102007007915 | 8/2008 |
| EP | 0392951 | 10/1990 |
| EP | 2065017 | 6/2009 |
| JP | 2010-538707 | 12/2010 |
| WO | WO 97/07928 | 3/1997 |
| WO | WO 0044294 | 8/2000 |
| WO | WO 2005/070129 | 8/2005 |
| WO | WO 2008/023708 | 2/2008 |
| WO | WO 2008/034276 | 3/2008 |
| WO | WO 2008/095327 | 8/2008 |
| WO | WO 2008/101090 | 8/2008 |
| WO | WO 2008/102428 | 8/2008 |
| WO | WO 2008/116203 | 9/2008 |
| WO | WO 2008/128588 | 10/2008 |
| WO | WO 2009/003294 | 1/2009 |
| WO | WO 2009/029908 | 3/2009 |
| WO | WO 2009/036576 | 3/2009 |
| WO | WO 2009/117837 | 10/2009 |
| WO | WO 2009/132472 | 11/2009 |

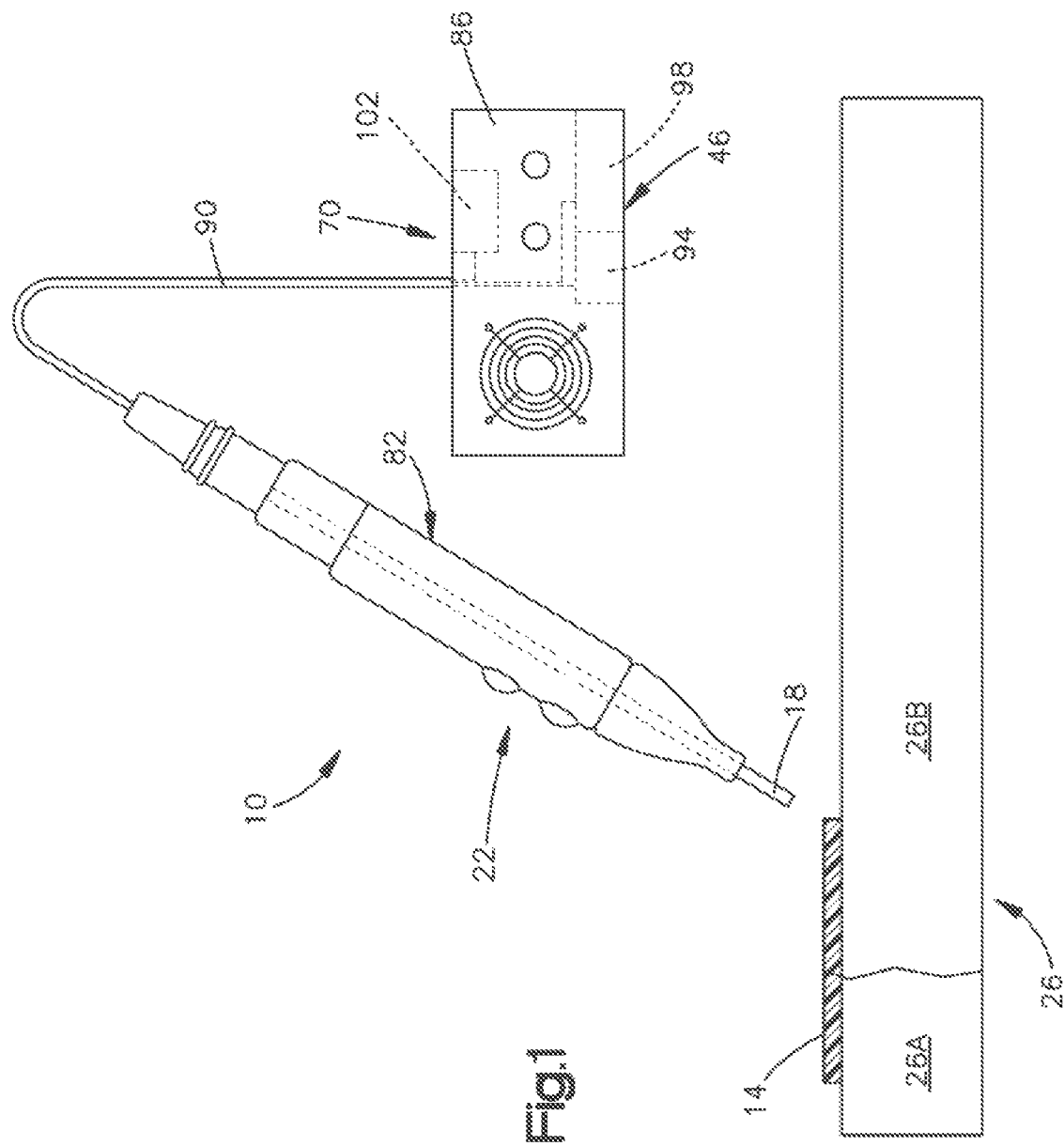

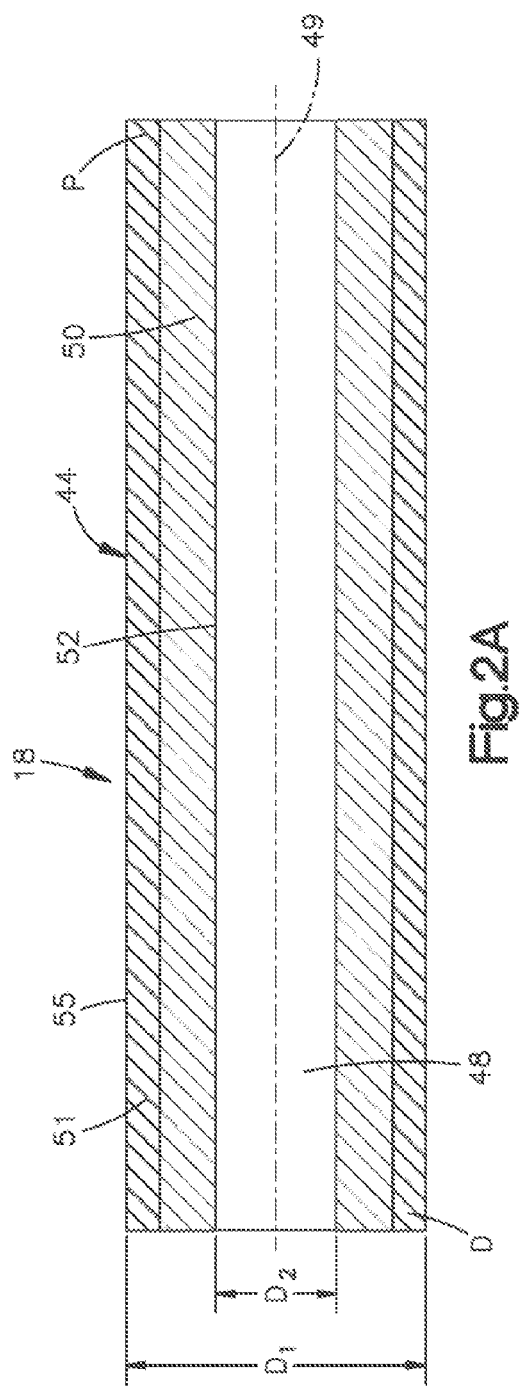
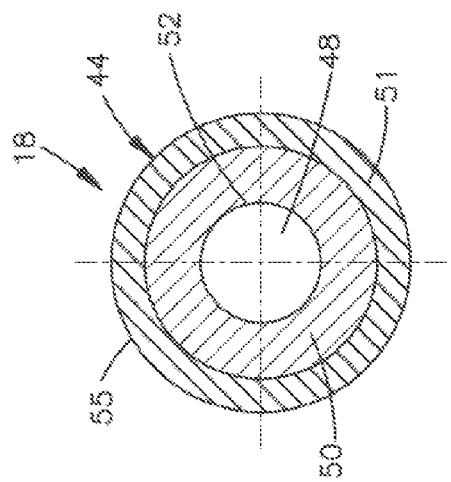
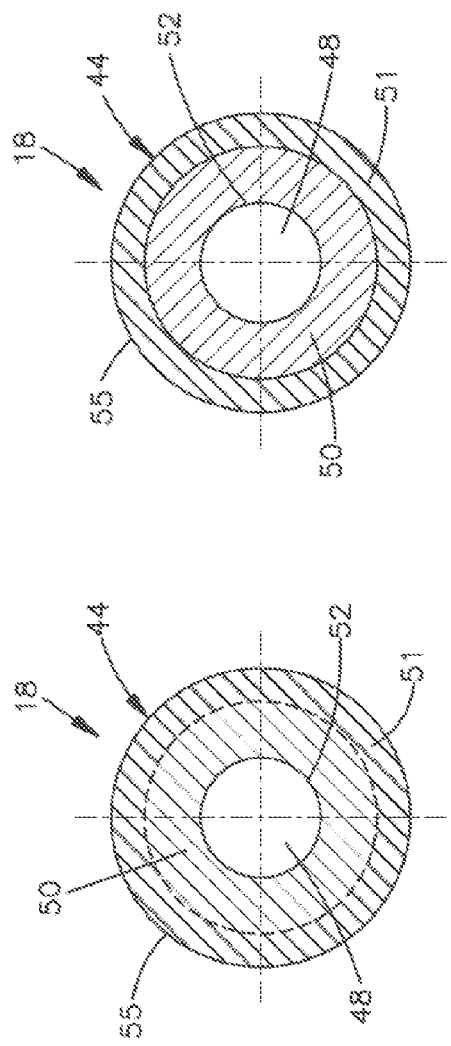

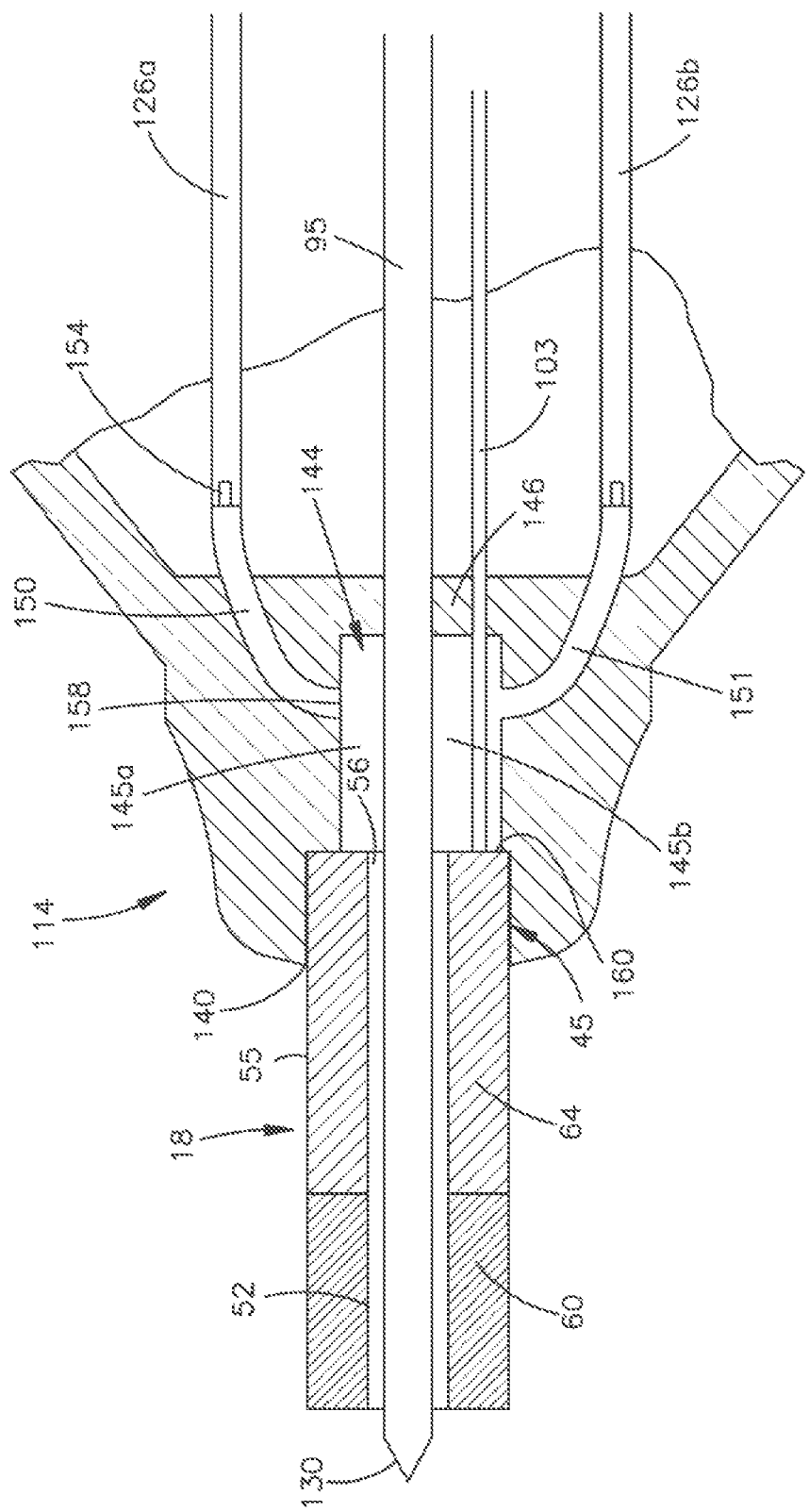

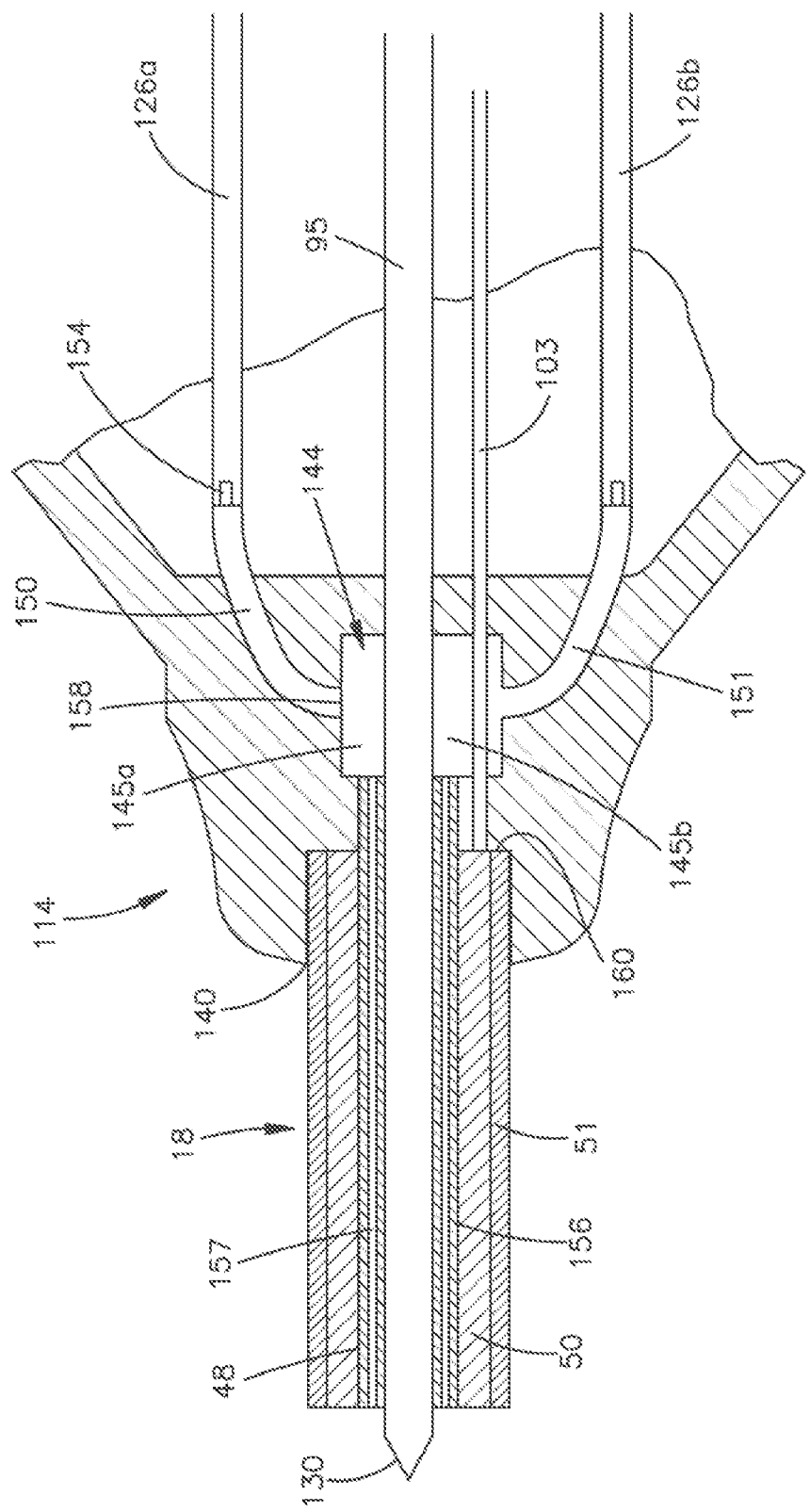

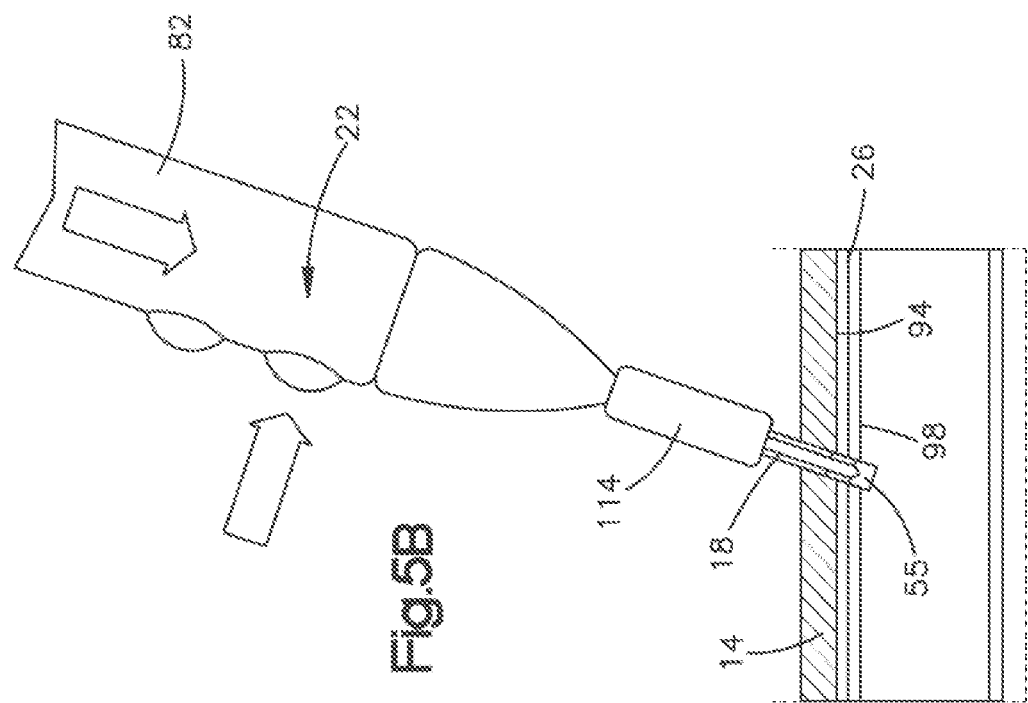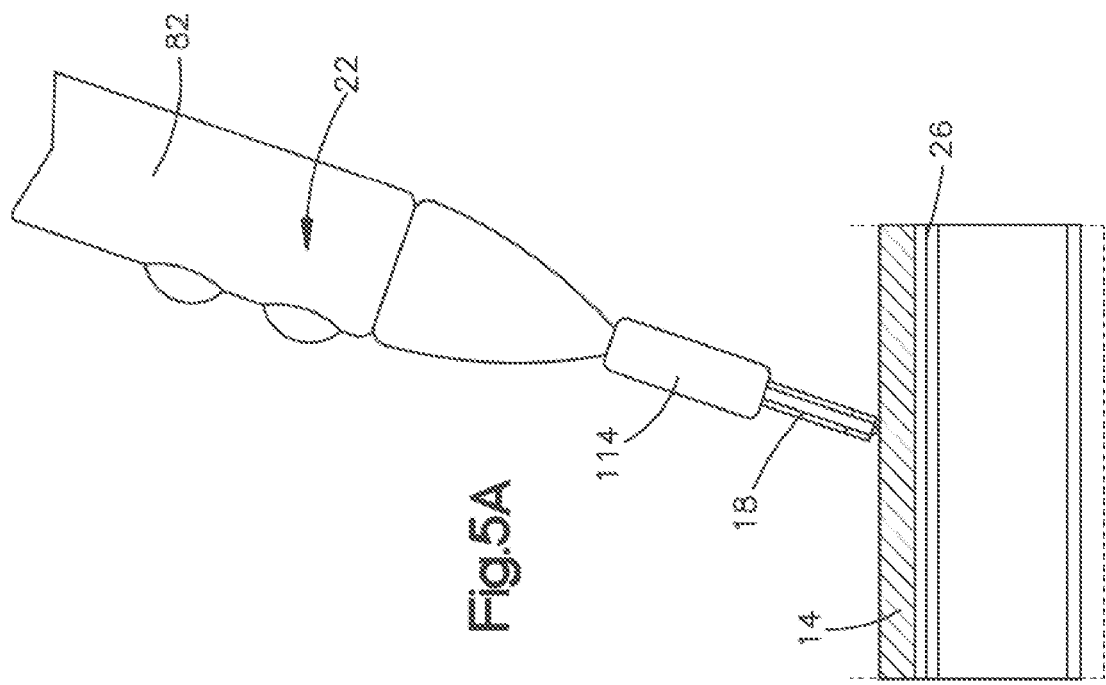

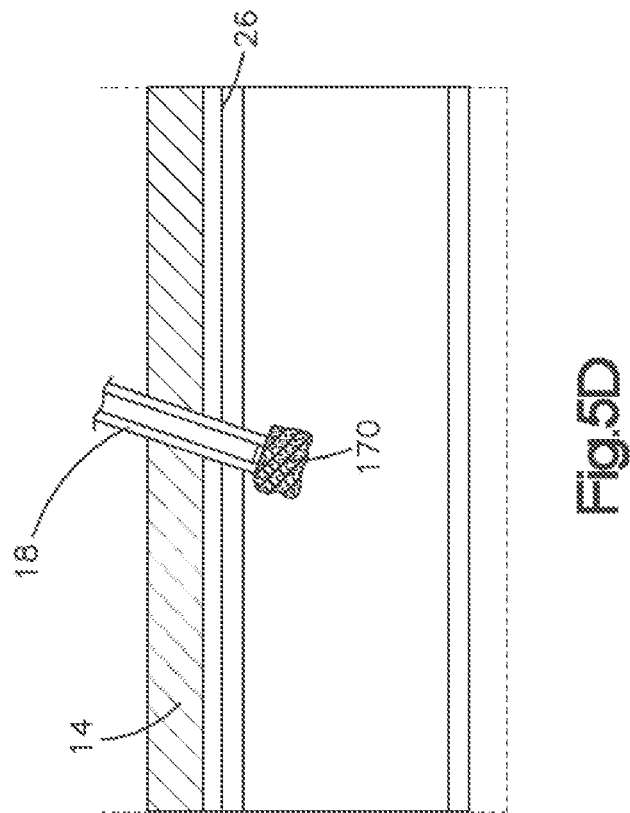
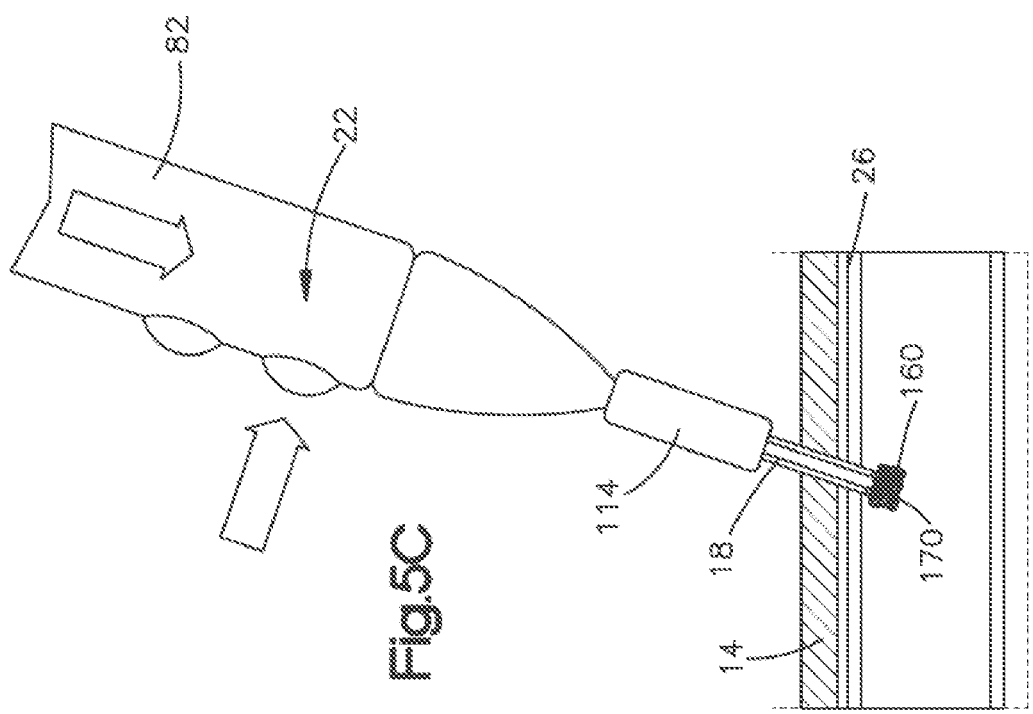

BONE FIXATION SYSTEM

CROSS REFERENCE TO RELATED APPLICATIONS

This application is a divisional of U.S. patent application Ser. No. 14/694,075, filed Apr. 23, 2015, which is a divisional of U.S. patent application Ser. No. 13/078,188, filed Apr. 1, 2011, which claims the benefit of U.S. Provisional Patent Application Ser. No. 61/417,614 filed Nov. 29, 2010, and further claims the benefit of U.S. Provisional Patent Application Ser. No. 61/320,883 filed Apr. 5, 2010, the disclosures of all of which are hereby incorporated by reference as if set forth in their entirety herein.

BACKGROUND

Fractured bones are a common injury seen in trauma centers. Surgeons in trauma centers frequently encounter many different types of fractures with a variety of different bones. For stabilizing a bone fracture, a metal fixation plate with suitable holes is fixed to bone fragments on opposing sides of the fracture using metal screws or pins. Typically the screws are self-cutting and are rotated into threadless openings in the bone, or they are screwed into pre-drilled threaded openings. Fracture fixation using such plates and screws may include several procedural steps and several instruments. For example, a first instrument may be used to cut the holes in the bone, and then a second instrument may be used to place the screws or pins. Therefore, the complexity and duration of the surgery may be unnecessarily lengthy and complex.

SUMMARY

Disclosed is a surgical fastener may include a body that includes a first portion and a second portion. The body may define a bore that extends through at least the first portion along a longitudinal axis of the body. The bore may be configured to receive a cutting mechanism. The first portion of the body may be transmissive to electromagnetic radiation and the second portion of the body may be absorptive to electromagnetic radiation such that upon absorbing electromagnetic radiation the second portion of the body softens and is capable of deforming. In one embodiment, the body defines a proximal end and a distal end spaced from the proximal end along the longitudinal axis, the proximal end is configured to attach to a surgical device that emits an energy source, and the first portion is disposed proximally with respect to the second portion. In another embodiment, the first portion may be an inner core portion and the second portion may be an outer peripheral portion.

The surgical fastener may be part of a kit that includes both a bone plate and at least one polymer based fastener. The bone plate may be comprised of a thermoplastic material. The fastener may include a body that defines a first portion, and a second portion. The second portion may have laser absorbing properties. The fastener may also include a bore that extends through at least the first portion of the body. The bore may be configured to receive a cutting mechanism.

Also disclosed is a surgical device configured to implant a surgical fastener into a target anatomical location. The surgical device may include a hand piece having a body that is configured to support a fastener that has a body and a bore that extends through the body. The surgical device may also include a cutting mechanism and an energy source. The cutting mechanism may be configured to extend through the bore of the fastener and cut into a target anatomical location. The energy source may be configured to heat and soften a portion of the fastener.

Also disclosed is a method of fixation of a surgical fastener to a target anatomical location. According to the method a hole may be cut into the target anatomical location by using a cutting mechanism of a surgical device. A fastener that is attached to a tip of the surgical device may be advanced into the hole of the boney structure as the cutting mechanism is cutting the hole. An energy source of the surgical device may then be activated to thereby heat the fastener so as to soften at least a portion of the fastener. Once finished the surgical device may be removed while the fastener remains attached to the boney structure.

BRIEF DESCRIPTION OF THE DRAWINGS

The foregoing summary, as well as the following detailed description of preferred embodiments of the application, will be better understood when read in conjunction with the appended drawings. For the purposes of illustrating the surgical fasteners and devices of the present application, there is shown in the drawings preferred embodiments. It should be understood, however, that the application is not limited to the precise arrangements and instrumentalities shown. In the drawings:

FIG. 1 is a schematic view showing a surgical device fixating a bone plate to bone with a surgical fastener;

FIG. 2A is a longitudinal cross-sectional view of a surgical fastener according to one embodiment, the surgical fastener having a core portion and a peripheral portion capable of deforming;

FIG. 2B is a transverse cross-sectional view of the surgical fastener shown in FIG. 2A, the core portion and the peripheral portion are joined such that the surgical fastener is configured as a one-piece fastener;

FIG. 2C is a transverse cross-sectional view of the surgical fastener shown in FIG. 2A, the peripheral portion being a coating disposed on the core portion;

FIG. 4C is a detailed side view illustrating the tip of the device shown in FIG. 4A holding a surgical fastener for affixing a bone plate to bone;

FIG. 4D is a detailed side view illustrating the tip of the device shown in FIG. 4A holding another embodiment of the surgical fastener for affixing a bone plate to bone;

FIG. 5A is a schematic view of a surgical device being positioned to affix a bone plate to bone;

FIG. 5B is a schematic view of the surgical device shown in FIG. 5A activating a first laser to drill through the bone plate and bone, and simultaneously advancing a surgical fastener;

FIG. 5C is a schematic view of the surgical device shown in FIG. 5B activating a second laser to soften at least a portion of the surgical fastener; and FIG. 5D is a schematic view showing the surgical fastener affixing the bone plate to bone after the surgical device is removed.

DETAILED DESCRIPTION

Figure 3B:
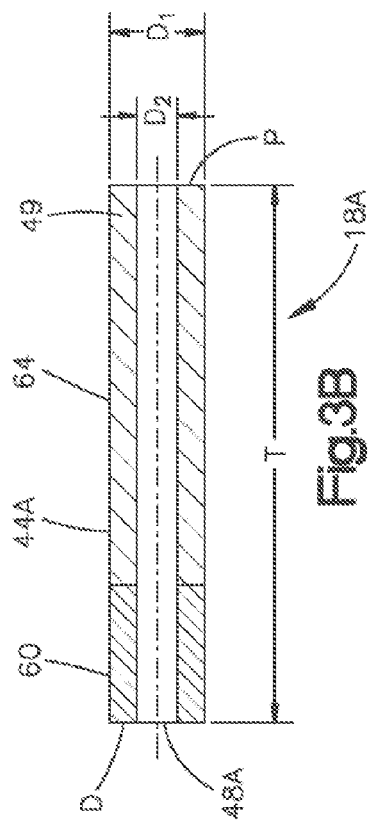
FIG. 3B is a longitudinal cross-sectional view of the surgical fastener shown in FIG. 3A.

Referring to FIG. 1, a bone fixation system 10 includes a plate 14, one or more fasteners 18 configured to attach the plate 14 to a target anatomical location such as bone 26, and a surgical device 22 that facilitates the attachment of the plate 14 and the fasteners 18. It should be appreciated that the bone 26 can include two or more fractured bone segments, such as bone segments 26A and 26B, or can include any other deformity amenable to treatment using bone fixation. Moreover, the target anatomical location may be structure other than bone, such as ligaments, and other soft or hard tissue structures. As shown, the plate 14 is placed over or onto the bone 26, and the surgical device 22 may be positioned over the plate 14 to cut a hole in either the plate 14, the bone 26, or both, so as to affix the plate 14 to the bone 26 using the fastener 18. The fixation of the plate 14 using one or more fasteners 18 and the surgical device 22 may be performed using a single device. For instance, only a single device 22 can be used to cut a hole, place the fastener 18, and affix the plate 14 to the bone 26 with the one or more fasteners 18. It should be understood that the entire fixation system 10 may be sold as a kit or alternatively, the plate 14, and the one or more fasteners 18 may be sold as a kit themselves. For instance, a plurality of fasteners 18 having different sizes and/or shapes can be provided as a kit.

Alternatively or additionally, a plurality of plates 14 having different sizes and/or shapes can be provided as a kit. Alternatively or additionally still, a combination of fasteners 18 and plates 14 having the same or different sizes and/or shapes can be provided as a kit, either alone or in combination with the surgical device 22. Furthermore, while the fasteners 18 are illustrated as pins, they can alternatively be provided as screws having threaded surfaces, nails having smooth or toothed surfaces, bolts, or any alternative fixation device configured to fix the bone plate 14 to the underlying bone 26.

As shown in FIG. 1, the surgical device 22 includes a hand piece 82, and a control unit 86 that is connected to the hand piece 82 by a cord 90. The control unit supplies a cutting mechanism 46 that is configured to cut the holes into the plate 14 and the bone 26, and an energy source 70 that is configured to heat and soften the fasteners 18 to thereby attach the plate 14 to the bone 26. The cutting mechanism 46 may include a first laser 94 and an irrigation system 98, and the energy source 70 may include a second laser 102. The first laser 94, the irrigation system 98 and the second laser 102 are arranged in the control unit 86 and delivered to the hand piece 82 of the surgical device 22 through the cord 90.

The plate 14 provides a load bearing structure that can be connected to bone fragments. The plate 14 is preferably made from a polymer material. For example the plate 14 may be made from poly-alpha-hydroxyester, polyorthoester, polyanhydride, polyphosphazenes, poly(propylenefumarate), polyesteramide, polyethylenefumarate, polylactide, polyglycolide, polycaprolacton, trimethylenecarbonate, polydioxanone, polyhydrobutyrate, as well as their copolymers and mixtures. The plate 14 may also include electromagnetic radiation absorption properties. For example, the plate 14 may include an additive, such as chlorophyll, carbon black, iron oxide, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, and D&C yellow No. 10, which allows the plate 14 to absorb energy such as heat from the second laser 102. In operation, the portion of the plate 14 that has the electromagnetic radiation absorption properties, absorbs the laser beam and deforms, thereby contributing to the fixation of the plate 14 to the bone 26. In another embodiment, the electromagnetic radiation absorbing component may include magnetic nano-particles, and the second laser 102 may be replaced by an electromagnetic transmitter that emits an electromagnetic signal in the range of 20 kHz to 10 GHz. Alternatively, ultrasonic vibrations, a conventionally heated metal bolt or heated air flow might be used for melting the fastener/plate.

Further, the plate 14 may be provided without predrilled holes and thus may define a continuous surface between opposing edges along a length that defines a target location for the insertion of one or more of the fasteners 18. During installation, the cutting mechanism of the surgical device 22 may be used to produce holes in the plate 14. It should be understood, however, that the plate 14 is not limited to plates defining continuous surfaces, and may be provided with predrilled holes. Furthermore, it should be understood by one of skill in the art, that the plate 14 and the holes may be provided in a variety of shapes and sizes.

As shown in FIGS. 2A-2C each surgical fastener 18 includes a body 44 that is elongate in a longitudinal direction L and defines a distal end D and a proximal end P. Each surgical fastener 18 further includes a bore 48 that extends through the body 44 in the longitudinal direction L and along a longitudinal axis 49 that may define a central axis of the fastener 18. In this way, the body 44 is tubular having an outer diameter D1 that defines an external surface 55 of the body 44, and an inner diameter D2 that defines an internal surface 52 of the body 44. As shown, the body 44 may be separated into a first or core portion 50 adjoining the internal surface 52, and a second or peripheral portion 51 adjoining the external surface 55.

The body 44 of the fastener 18 is made from a thermoplastic material, for example poly-alpha-hydroxyester, polyorthoester, polyanhydride, polyphosphazenes, poly(propylenefumarate), polyesteramide, polyethylenefumarate, polylactide, polyglycolide, polycaprolacton, trimethylenecarbonate, polydioxanone, polyhydrobutyrate, as well as their copolymers and mixtures. The peripheral portion 51 of the body 44 adjoining the external surface 55 is colored sufficiently to include electromagnetic radiation absorption properties while the core portion 50 of the body 44 adjoining the internal surface 52 is transmissive to the electromagnetic radiation provided by the energy source. For example, the colored peripheral portion 51 may include an additive, such as chlorophyll, carbon black, iron oxide, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, and D&C yellow No. 10, which allows absorption of electromagnetic radiation provided by the second laser 102.

By absorbing the energy of the second laser 102, the thermoplastic material of the peripheral portion 51 heats up and softens. That is, the softening of the fastener 18 occurs by the heat generated by the absorption of radiation from the second laser 102, to the point that allows the fastener 18 to be deformed. In particular, the additive, and in some cases some of the thermoplastic itself absorbs the laser and heats up to thereby cause the thermoplastic to soften. The softened thermoplastic material is capable of deforming and expanding into the hollow spaces of the bone tissue thereby affixing the fastener 18 and the plate 14 to the bone 26. The peripheral portion 51 may absorb at least twice as much irradiated energy as the core portion 50. Typically, however, a factor of 5-1000 times more energy is absorbed in the peripheral portion 51 with respect to the core portion 50. In other words, the peripheral portion 51 may absorb 50-100% of the energy, while the core portion 50 absorbs 0-10%. The thickness of the peripheral portion 51 is preferably over 0.1 mm and/or between 1 to 20% of the outer diameter D1. It should be understood that the peripheral portion 51 is not limited to thermoplastic materials capable of absorbing the second laser 102 and that other materials may be used. For example, the peripheral portion 51 may include magnetic nano-particles, and the laser can be replaced by an electromagnetic transmitter that emits an electromagnetic signal in the range of 1 kHz to 1 MHz or 100 KHz to 100 GHz.

The core portion 50 of the fastener 18 which is transmissive to the electromagnetic radiation may be configured so as not to warm-up at all or only partially, and to maintain its mechanical strength. At the same time, the core portion 50 can serve as an optical element and transmit the energy onward into the bone plate 14. The fastener 18 can then be pushed into a previously produced hole which may be undersized, and the warmed-up, softened polymer is then pressed into the interspaces of the bone. After turning off the energy source, the polymer (thermoplastic material) cools off and quickly hardens (<1-2 minutes), and the mechanical interdigitation between the fastener 18 and the bone and/or the bone plate 14 is established.

The core portion 50 and the peripheral portion 51 may be separate discrete components that are coupled together with the peripheral portion 51 e.g. being a coating that includes the electromagnetic radiation absorbing properties as shown in FIG. 2C, or they may be integral and thus one component, with the peripheral portion 51 comprising a chromophore (i.e. color or pigment) as shown in FIG. 2B. Further, in some embodiments, the peripheral portion 51 may be a zone with a variable absorption coefficient "a". In any case, the peripheral portion 51 includes the electromagnetic radiation absorbing properties sufficient to cause the peripheral portion 51 to deform in response to exposure to the first laser 94, while the region of thermoplastic material of the core portion 50 has a transparency to the second laser 102 that is greater than that of the peripheral portion 51. Therefore, the inner uncolored core portion 50 substantially maintains its structural integrity when exposed to the first laser 94 that deforms the peripheral portion 51.

As shown in FIGS. 3A-3D, in another embodiment, a fastener 18A includes a body 44A having first and second portions that are aligned with respect to a direction that extends substantially parallel to the longitudinal axis 49. As shown in FIG. 3B, the body 44A of the fastener 18A may include a first axial portion 64 and a second axial portion 60 disposed distally with respect to the first portion 64. The first portion 64 may be transmissive to electromagnetic radiation, while the second portion 60 may be configured to absorb electromagnetic radiation.

As with the fastener 18, fastener 18A may be made from a thermoplastic material. For example each fastener 18A may be made from poly-alpha-hydroxyester, polyorthoester, polyanhydride, polyphosphazenes, poly(propylenefumarate), polyesteramide, polyethylenefumarate, polylactide, polyglycolide, polycaprolacton, trimethylenecarbonate, polydioxanone, polyhydrobutyrate, as well as their copolymers and mixtures. The second axial portion 60 can be colored throughout its complete volume, and includes electromagnetic radiation absorption properties that allow the second portion to absorb energy provided by for example the laser 102, and the first axial portion 64 is transmissive to the energy provided by the laser 102. For example, the colored second portion 60 may include an additive, such as chlorophyll, carbon black, iron oxide, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate (2-)] copper, D&C blue no. 2, D&C blue no. 6, D&C green no. 6, D&C violet no. 2, and D&C yellow No. 10, which allows absorption of electromagnetic radiation provided by the second laser 102. In operation, the thermoplastic material in the complete volume of the second axial portion 60 of the fastener 18A absorbs the laser beam and deforms, thereby affixing the plate 14 to the bone 26. In another embodiment the second axial portion 60 may include magnetic nano-particles, and the first laser may be replaced by an electromagnetic transmitter that emits an electromagnetic signal in the range of 20 kHz to 10 GHz.

The first axial portion 64 and the second axial portion 60 may be separate discrete components that are coupled together, or they may be integral and thus one component, with the second axial portion 60 having a coating that includes the electromagnetic radiation absorbing properties. In either case, the second axial portion 60 includes the electromagnetic radiation absorbing properties sufficient to cause the second axial portion 60 to deform in response to exposure to an energy source such as the laser beam 102, while the thermoplastic material of the first axial portion 64 has a transparency to the laser beam 102 that is greater than that of the second axial portion 60, such that the uncolored first axial portion 64 substantially maintains its structural integrity when exposed to the laser beam 102 that deforms the second axial portion 60. The second axial portion 60 is shown in FIG. 3B as being disposed at the distal end "D" of the body 44, and the first axial portion 64 is illustrated as being disposed proximal with respect to the second axial portion 60. The colored second axial portion 60 may be from 10 to 80% of the overall length of the fastener 18A along the longitudinal direction.

Figure 3C:
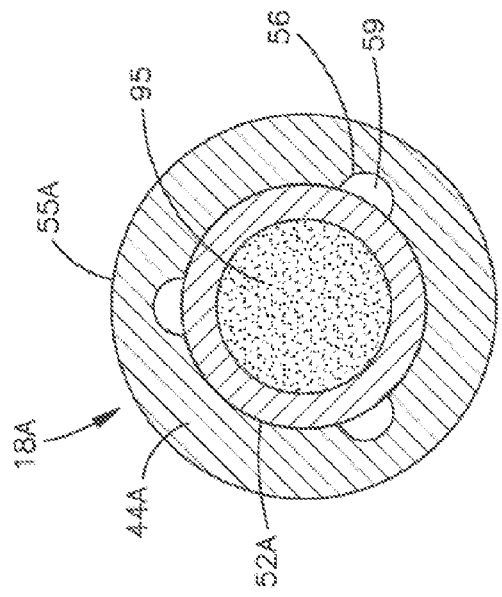
FIG. 3C is a transverse cross-sectional view of the surgical fastener shown in FIG. 3A, including an optical waveguide extending through the bore of the fastener.
Figure 3A:
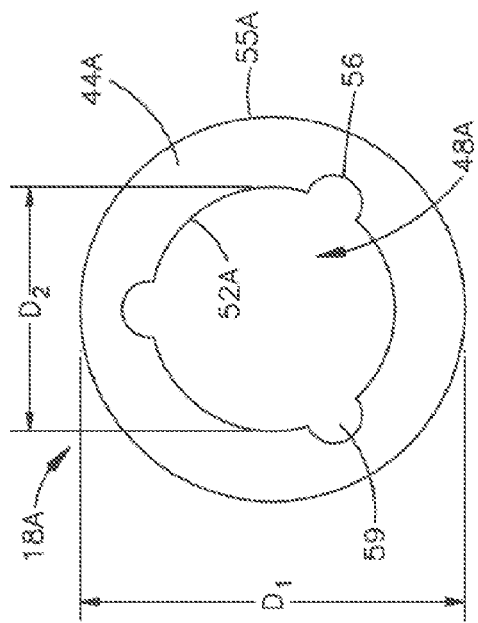
FIG. 3A is a front elevational view of a surgical fastener in accordance with another embodiment, the surgical fastener having a distal portion capable of deforming.
Figure 3D:
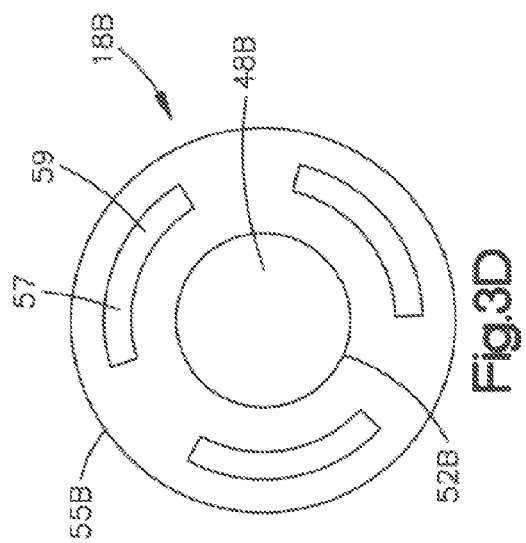
FIG. 3D is a front elevational view of a surgical fastener in accordance with another embodiment, the surgical fastener including closed irrigation channels.

As shown in FIGS. 3A-3D, the fasteners may be provided with irrigation channels 59 configured as recesses 56 or closed passages 57 as illustrated in FIGS. 3A and 3D. As shown in FIGS. 3A and 3B, a fastener 18A includes a hollow-cylindrical body 44A that is elongate along a longitudinal axis 49. The body 44A includes an external surface 55A that defines an outer diameter D1. As shown, each fastener 18A includes a bore 48A that extends through the body 44A in the direction of the longitudinal axis 49. As shown, the bore 48A has an inner diameter D2 that defines an internal surface 52A of the body 44A. The body 44A further defines a plurality of irrigation channels 59 configured as recesses 56 that extend into the internal surface 52A along the entire length of the bore 48A from the proximal end P to the distal end D. While the body 44A is illustrated as defining three circumferentially equidistantly spaced recesses 56 (i.e. disposed at 120° when viewed in cross-section), the body 44A can include any number of recesses 56 as desired spaced circumferentially about the body 44A as desired. As shown in FIG. 3A, in cross-section, each recess 56 may be in the shape of a half circle and may be configured to receive and carry an irrigation fluid. Each recess 56 may have a radius of about 0.1 mm to about 0.5. The recesses 56 may be radially spaced apart from each other to provide a number of irrigations channels 59 that allow an irrigation fluid to be injected through e.g. two of the three irrigation channels 59 and to be sucked off through e.g. one of the three irrigation channels 59. It should be understood, however, that the recesses 56 are not limited to being half circles and may be any shape capable of receiving an irrigation liquid.

In another embodiment and as illustrated in FIG. 3D the fasteners may include irrigation channels 59 that are closed passages 57. As shown, a fastener 18B includes a tubular body 44B, a bore 48B that extends through the body 44B, and three circumferentially equidistantly spaced closed passages 57 that extend through the body 44B between an internal surface 52B and an external surface 55B of the body 44B, such that no communication to the bore 48B exists. While the body 44B is illustrated as defining three circumferentially equidistantly spaced passages 57, the body 44B can include any number of passages 57 as desired spaced circumferentially about the body 44B as desired.

The fasteners 18, 18A, and 18B may be provided in a variety of sizes. For example, the outer diameter D1 of each fastener may be between 1.5 and 5 mm and the bores of the fasteners may have a diameter D2 of about 0.4 mm to 3 mm. Furthermore, the fasteners may have a length T extending along the longitudinal axis 49 that is between about 3 mm and about 20 mm long. The dimensions provided are for illustrative purposes only, and it should be understood that the fasteners may include any dimension capable of affixing the plate 14 to the underlying bone 26.

The color material or particles may be worked into the polymer of the fasteners using a variety of methods. For example, color-containing polymer layers or implant elements can be produced in a so-called two-component injection molding process. In this case, the uncolored portion of the fastener is injected in a first phase, and after modifying the cavity in the injection mold, the color containing portion is injected in a second phase.

The layers of color-containing polymer may also be achieved by applying and drying the color and polymer containing solutions. It is in this case possible to achieve layers of color containing polymer by depositing and drying the color and polymer containing solutions, similar to a candle-drawing process (dip-coating process) or by spraying. The use of the first-mentioned depositing process allows achieving layers of a very thin (micrometer-thin) up to a very thick (sub- and millimeter range) size.

The color layer(s) may also be achieved by applying and drying color-particles containing suspension or solution. In this case, the coating occurs by first warming-up the color-containing particles. The heated particles may then be jetted onto the surface of the uncolored part of the fastener, so that the particles fuse with the polymer of the uncolored portion of the fastener and are fixated on the surface.

Ceramic or other non-thermally sensitive particles may also be applied to the surface by jetting them onto the polymer surface in a heated condition, where they can locally fuse with the polymer and be fixated in the surface. An example for this is given by the plasma spraying process by which hip joint prostheses are for instance coated with calcium phosphate particles. The use of processes such as Chemical Vapor Deposition (CVD) or Physical Vapor Deposition (PVD) is also conceivable in the presence of suitable substrates.

Figure 4A:
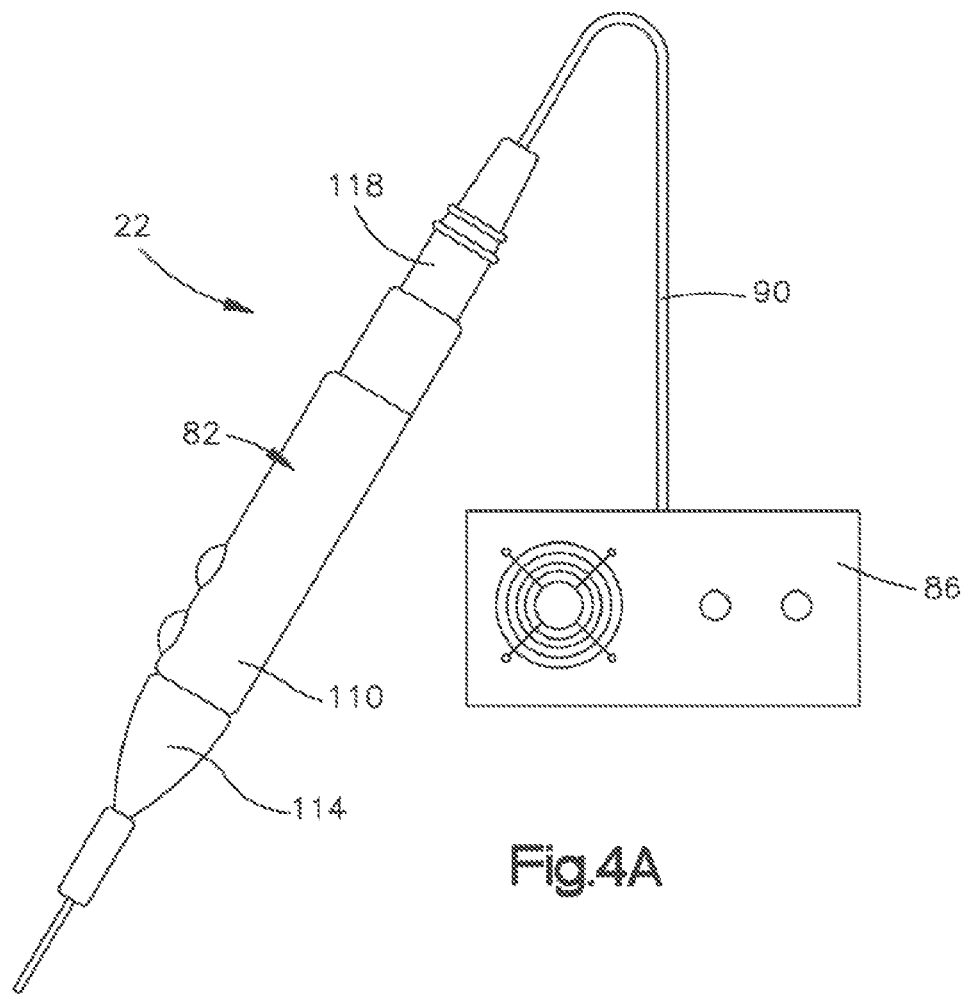
FIG. 4A is a side elevational elevation view of a surgical device configured to affix a bone plate to bone using a surgical fastener.
Figure 4B:
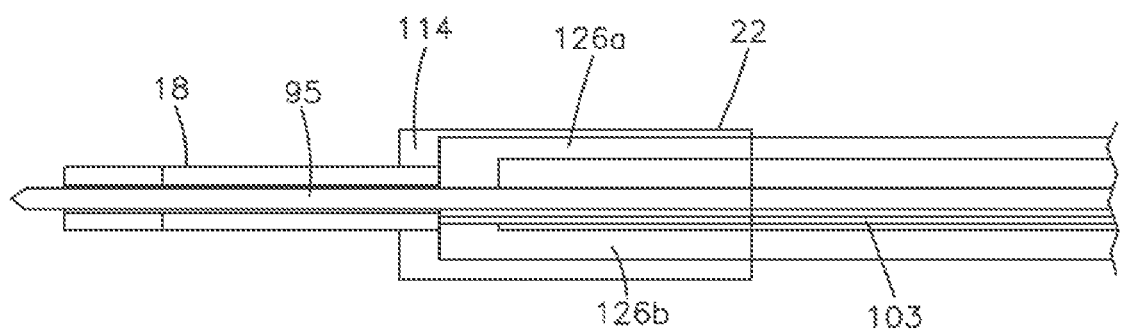
FIG. 4B is a schematic view showing a first laser, a second laser and an irrigation supply of the device shown in FIG. 4A.

Each fastener may be positioned and affixed to the plate 14 and the bone 26 using the surgical device 22 shown in FIGS. 4A-4C. As shown, the surgical device 22 includes a hand piece 82, a control unit 86, and a cord 90 connecting the hand piece 82 to the control unit 86. The surgical device 22 is a processing apparatus configured to provide both the cutting mechanism 46 and the energy source 70. In the embodiment shown, the cutting mechanism includes a first laser 94 and an irrigation supply 98 that is connected to a first optical waveguide 95, while the energy source 70 includes a second laser 102 that is connected to a second optical waveguide 103. The first laser 94 and irrigation supply 98 may be configured to cut through the plate 14, the bone 26, or both, and the second laser 102 may be configured to heat and deform the second axial portion 60 or the tubular peripheral portion 51 of the fasteners 18, 18A, and/or 18B. The irrigation supply 98 is configured to supply a coolant liquid and to remove the debris from the cutting site. The optical waveguides 95, 103 may be flexible or rigid optical light-transmitting structures, such as for instance glass fiber cables or reflecting hoses (e.g. also nano-tubes) used to transmit electromagnetic radiation from the source to the fastener. On the other hand, the fastener itself may serve as an optical fiber and light diffuser. After entering the fastener, the light is transmitted through the first portion of the fastener until it arrives at the point where the softening of the polymer, mostly at its surface, is to take place. In order to transmit the light through the optical fiber to the fastener up to the desired point, the fastener may on one hand actually transmit the light, meaning for instance to the tip of a pin and then distribute it there, so as to reach the surface of the fastener, for instance by diffusion.

In one embodiment, the first laser 94 is a 3 μm infrared laser, the irrigation supply 98 uses a liquid such as water, and the second laser 102 is an 800 nm infrared laser. It should be understood, however, that the device 22 is not limited to a cutting mechanism 46 comprising the 3 μm infrared laser, and water supply, nor is it limited to an energy source 70 comprising the 800 nm infrared laser. For example, the cutting mechanism 46 may also be a 10 μm $CO_2$ laser combined with an irrigation supply, or a 2.8 μm Erbium YAG laser combined with an irrigation supply. Similarly, the second laser 102 may be a laser having a wave length in the range of 400 nm to 1800 nm or it may be replaced by an electromagnetic transmitter in the range of 20 kHz to 10 GHz, or both infrared lasers may be replaced by an ultrasonic source capable of both: (i) cutting through the plate 14, and the boney structure 26, and (ii) heating and thereby softening the fastener 18.

The control unit 86 includes each of the first laser 94, the irrigation supply 98, and the second laser 102. The control unit 86 can include settings that are controlled by a user to determine the operation of the bone fixation system. For example, a user may at first set the control unit 86 to simultaneously supply the first laser 94, and the irrigation supply 98, to cut through the plate 14 and the bone 26, and then mid-procedure, change the control unit 86 to supply the second laser 102 to deform the fastener 18.

As shown in FIGS. 1, and 4A-4C, the hand piece 82 includes an elongated body 110 having a tip 114 at its distal end and a connecting portion 118 at its proximal end for connecting the body 110 to the cord 90. The elongated body 110 is generally a tube-like structure that is constructed to contain said first and second waveguides 95, 103 and/or irrigation tubes 126a, 126b, as shown in FIG. 4C. The first and second optical waveguides 95, 103 may be optical fibers, which are configured to transmit the beams of the first and second laser 94 and 102 from the control unit 86 through the body 110 and to the tip 114. Similarly, the irrigation tubes 126 are configured to transport the irrigation liquid from the control unit 86 through the body 110 and to the tip 114 and to suck the irrigation fluid off in the reverse direction, and can thus also be referred to as irrigation tubes. A fiber tip end 130 proximate to the distal end of the fastener disperses the beam of the first laser 94 as desired so as to allow the hole that is cut into the plate 14 and bone 26 to have a diameter that allows the fastener to pass through. The fiber tip end 130 can give way several mm back into the device 22, to enable compression of the second axial portion 60 of the fastener inside the boney structure 26. For example, as the fastener is compressed down by a user, the fiber tip end 130 may be retracted proximally either by translating proximally with respect to the handle, or by compressing, as a portion of such as the axial portion 60 of the fastener 18A compresses or otherwise deforms.

Referring also to FIG. 3C, the first optical waveguide 95 is configured to extend through the bore 48 of the body 44 of the fastener 18. In particular, the first optical waveguide 95 defines a diameter that is substantially equal to the diameter of the bore 48. Thus, the bore 48 of the fastener 18 is sized to receive the first optical waveguide 95 that guides the beam of the first laser 94 such that there is little clearance between the first optical waveguide 95 and the internal surface 52 of the bore 48. As a result, the first optical waveguide 95 substantially closes the inner radial ends of each of the recesses 56 so as to define a plurality of irrigation channels 59, which extend along the length of the fastener 18.

FIG. 4C illustrates a tip 114 configured to be used with a fastener such as fastener 18, as shown in FIG. 2A, and fasteners 18A, and 18B including irrigation channels 59 as shown in FIGS. 3A and 3D. The tip 114 is configured to grip and hold or otherwise support the fasteners. The proximal end P of the fastener 18 can comprise an attachment portion 45 that can be e.g. configured as a cylindrical portion dimensioned for a press fit with a corresponding bore 140 in the tip 114. As shown, the tip 114 includes a channel 144 extending from a wall 146 and toward the distal end of the tip 114, and a bore 140 that extends proximally from the distal end of the tip 114 in alignment with the channel 144. The bore 140 defines a diameter greater than that of the channel 144, such that the tip 114 provides a seat 148 at the interface between the bore 140 and the channel 144. The interface abuts and supports the fastener 18 at the distal end of the channel 144 when the fastener 18 is fully inserted or otherwise disposed in the bore 140. The channel 144 is separated into an injection segment 145a for injecting an irrigation liquid and a suction segment 145b allowing to suck off the irrigation liquid together with the debris. The hand piece body 110 further includes a first and a second port 150, 151 extending into the tip 114. Each of the first and second ports 150, 151 has a coupling 154 at its proximal end for coupling an irrigation tube 126a, 126b thereto and an opening 158 at its distal end. The openings 158 of the first and second port 150, 151 extend into the channel 144 so as to place the channel 144 in fluid communication with the couplings 154 of the first and second port 150, 151.

The bore 140 is sized to receive and hold a fastener such as fasteners 18A or 18B as described above, and the channel 144 is configured to guide the irrigation liquid of the irrigation supply 98 from the port opening 158 to two irrigation channels 59 of the fastener which can be recesses 56 or closed passages 57 and to suck the irrigation fluid and the debris off through the third irrigation channel 59 of the fastener 18.

A first irrigation tube 126a is connected to the coupling 154 of the first port 150, and the irrigation liquid of the irrigation supply 98 travels through the first irrigation tube 126a, into the injection segment 145a of the channel 144 via the first port 150 and through two irrigation channels 59 of the fastener. A second irrigation tube 126b is connected to the coupling 154 of the second port 151, and the irrigation fluid with the debris can be sucked off through the third irrigation channel 59 of the fastener 18 defined by the third irrigation channel 59 into the suction segment 145b of the channel 144 and via the second port 151 into the second irrigation tube 126b.

The beam of the first laser 94 and the irrigation liquid of the irrigation supply 98 may simultaneously travel longitudinally through the fastener 18A and out the distal end D of the fastener 18A to thereby cut the hole into the plate 14 and/or the bone 26. As shown, the beam of the second laser 102 may be guided to a front or proximal wall 160 of the fastener 18A. When the second laser 102 is activated, the light travels through the transparent first axial portion 64 of the fastener 18A, and is absorbed by the laser absorbing second axial portion 60. Alternatively, when using a fastener 18 according to FIGS. 2A to 2C the light travels through the thermoplastic material in the core portion 50 and is absorbed by the laser absorbing colored thermoplastic material of the peripheral portion 51 adjoining the external surface 55 of the fastener 18, and by the adjacent portion of the plate 14.

The tip 114 may be a sterile single use part that may consists of a fastener, such as anyone of fasteners 18, 18A, or 18B and the fiber tip end 130 that is configured to adequately cut through the bone 26 (note that the fiber tip end may be shaped in a way to disperse the laser beam, so that it is actually possible to drill a hole that is large enough to fit the fastener—which is larger than the fiber tip. The single use part may be configured to be selectively attached to or detached from a distal end of the body 110. The single use part may also be made from a material that is capable of being placed in an autoclave.

FIG. 4D illustrates another embodiment of the tip 114 configured to be used with a fastener 18 as illustrated in FIGS. 2A to 2C. The embodiment of the tip 114 according to FIG. 4D differs from the embodiment of FIG. 4C only therein that the tip 114 comprises a sleeve 156 affixed to the tip 114 and comprising two or more bore holes 157 in fluid communication with the channel 144. The sleeve 156 can be inserted into the bore 48 of the fastener 18 and surrounds the first optical waveguide 95. The two or more bore holes 157 are arranged circumferentially equally spaced and suitable to guide the irrigation liquid of the irrigation supply 98 from the channel 144 to the tip 130. The channel 144 is separated into an injection segment 145a for injecting the irrigation liquid and a suction segment 145b allowing to suck off the irrigation liquid together with the debris. The injection segment 145a is configured to guide the irrigation liquid of the irrigation supply 98 from the port opening 158 through two or more bore holes 157 in the sleeve 156 that is inserted in the bore 48 of the fastener 18 and the suction segment 145b is configured to suck the irrigation fluid and the debris off through one or more of the bore holes 157 in the sleeve 156.

In operation and in reference to FIGS. 5A-5D the surgical device 22 may affix the plate 14 and the fastener 18 (or 18A or 18B) in a simple and efficient manner. As shown in FIG. 5A, the fastener 18 is placed into the tip 114 of the hand piece 82 such that the fastener 18 partially extends distally of the tip 114, and the plate 14 is positioned on the bone 26 over the fractured area. The hand piece 82 along with the fastener 18 may then be positioned on the surface of the plate 14 and at an angle of 90° with respect to the plate 14, or offset with respect to the 90° angle if desired. Once the hand piece 82 is positioned, the control unit 86 may be activated to cause the beam of the first laser 94 and the irrigation supply 98 to cut or drill a hole 55 through the plate 14 and into the bone 26 if desired. As shown in FIG. 5B, the first laser 94 and the irrigation liquid of the irrigation supply 98 travel through the bore 48 of the fastener 18 and out a distal end of the fastener 18. As the hole 55 is being cut, the hand piece 82 and thus the fastener 18 may be gently pushed into the hole as it is created over time.

Once the desired depth of the hole is reached and the fastener 18 is properly positioned within the hole, the control unit 86 may be switched to deactivate the first laser 94 and the irrigation supply 98, and activate the second laser 102 to thereby deform a portion of the fastener 18. As shown in FIG. 5C, the beam of the second laser 102 may soften and deform the fastener 18 and the interface between the plate 14 and the fastener 18. A gentle push of the device 22 in the direction of said longitudinal axis 49 into the hole 55 causes a portion of the fastener 18 to deform and define an outer dimension that is greater than that of the hole 55. Thus, the fastener 18 transforms into a rivet 170 that couples the plate 14 to the bone 26.

The bone fixation procedure described above can be performed to fix the bone plate 14 to one or more bone segments of the bone 26 that are separated by a fracture. For instance, the bone plate 14 is positioned over the fracture site or fracture sites, and one or more fasteners can couple the plate 14 to each bone segment in the manner described above.

As shown in FIG. 5D, the device 22 may be removed, while the plate 14 and fastener 18 remain behind. The plate 14 and fastener 18 may be made from a resorbable material.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. Moreover, any of the embodiments described above can incorporate any structures or features of any of the other embodiments described above, as desired. Those skilled in the relevant art, having the benefit of the teachings of this specification, may effect numerous modifications to the invention as described herein, and changes may be made without departing from the spirit and scope of the invention as defined by the appended claims.

What is claimed is:

1. A method of fixing a surgical fastener to a target anatomical location, the method comprising steps of:
    directing a laser of a cutting mechanism of a surgical device toward the target anatomical location so as to cut a hole in the target anatomical location;
    advancing the surgical fastener into the hole of the target anatomical location as the surgical fastener is supported by the surgical device;
    activating an energy source of the surgical device to thereby heat and soften at least a portion of the surgical fastener so as to attach the surgical fastener to the target anatomical location; and
    removing the surgical device while the surgical fastener remains attached to the target anatomical location.

2. The method according to claim 1, wherein:
    the cutting step includes:
        placing a polymer based bone plate on the target anatomical location;
        cutting a hole through the plate and into the target anatomical location by using the cutting mechanism of the surgical device; and
    the removing step comprises removing the surgical device while the surgical fastener and plate remain attached to the target anatomical location.

3. The method according to claim 1, further comprising:
    pressing the surgical fastener into the hole in the target anatomical location during heating and softening of the portion of the surgical fastener.

4. The method according to claim 1, comprising heating the surgical fastener to such a degree that the fastener becomes at least partially deformable.

5. The method of claim 1, wherein the advancing step comprises advancing the surgical fastener into the hole as the cutting mechanism cuts the hole.

6. The method according to claim 1, wherein the activating step comprises transmitting electromagnetic radiation from the energy source to the surgical fastener.

7. The method according to claim 6, wherein the activating step comprises transmitting the electromagnetic radiation through a transmissive portion of the surgical fastener to the portion of the surgical fastener.

8. The method of claim 7, wherein the activating step comprises transmitting the electromagnetic radiation through a core that defines the transmissive portion to an external surface of the surgical fastener that defines the portion.

9. The method of claim 7, wherein the activating step comprises transmitting the electromagnetic radiation through a proximal end of the surgical fastener that defines the transmissive portion to a distal end of the surgical fastener that defines the portion.

10. The method of claim 1, comprising a step of inserting the cutting mechanism into a bore that extends into a body of the surgical fastener such that the cutting mechanism supports the surgical fastener.

11. The method of claim 1, wherein the activating step comprises heating the surgical fastener with a laser of the energy source, the laser of the energy source being different from the laser of the cutting mechanism.

12. The method of claim 11, wherein the directing step comprises directing one of a 3 μm infrared laser, a 10 μm $CO_2$ laser, and a 2.8 μm Erbium YAG laser toward the target anatomical location.

13. The method of claim 11, the activating step comprises heating the surgical fastener with a 800 nm laser.

14. The method of claim 1, further comprising injecting an irrigation fluid into a recess in the surgical fastener as the cutting mechanism cuts the hole so as to remove debris from the hole.

15. A method of fixing a surgical fastener to a target anatomical location, the method comprising steps of:
    extending a cutting mechanism of a surgical device through a bore of the surgical fastener;
    cutting a hole in the target anatomical location as the cutting mechanism extends through the bore of the surgical fastener;
    advancing the surgical fastener into the hole of the target anatomical location as the surgical fastener is supported by the surgical device and as the cutting mechanism is cutting the hole;
    activating an energy source of the surgical device to thereby heat and soften at least a portion of the surgical fastener so as to attach the surgical fastener to the target anatomical location; and
    removing the surgical device while the surgical fastener remains attached to the target anatomical location.

16. The method according to claim 15, wherein:
the cutting step includes:
- placing a polymer based bone plate on the target anatomical location;
- cutting a hole through the plate and into the target anatomical location with the cutting mechanism of the surgical device; and the removing step comprises removing the surgical device while the surgical fastener and plate remain attached to the target anatomical location.

17. The method of claim 15, wherein the extending step comprises extending a first optical waveguide through the bore.

18. The method of claim 17, wherein the cutting step comprises directing a laser of the cutting mechanism of the surgical device toward the target anatomical location so as to cut the hole in the target anatomical location.

19. The method of claim 15, wherein the activating step comprises heating the surgical fastener with a laser of the energy source.

20. The method according to claim 15, wherein the activating step comprises transmitting electromagnetic radiation through a transmissive portion of the surgical fastener to the portion of the surgical fastener.

* * * * *